(12) United States Patent
Eisenhandler et al.

(10) Patent No.: US 8,579,811 B2
(45) Date of Patent: Nov. 12, 2013

(54) MEDICAL DIAGNOSIS DERIVED FROM PATIENT DRUG HISTORY DATA

(75) Inventors: Jon Eisenhandler, Bristol, CT (US); Richard F. Averill, Seymour, CT (US); Norbert I. Goldfield, Northampton, MA (US)

(73) Assignee: 3M Innovative Properties Company, Saint Paul, MN (US)

( * ) Notice: Subject to any disclaimer, the term of this patent is extended or adjusted under 35 U.S.C. 154(b) by 728 days.

(21) Appl. No.: 11/532,919

(22) Filed: Sep. 19, 2006

(65) Prior Publication Data

US 2008/0081955 A1 Apr. 3, 2008

(51) Int. Cl.
*A61B 5/00* (2006.01)
*G06F 19/00* (2011.01)
*G06Q 50/22* (2012.01)

(52) U.S. Cl.
CPC .......... *G06F 19/34* (2013.01); *G06F 19/3456* (2013.01); *G06F 19/322* (2013.01); *G06Q 50/22* (2013.01); *A61B 5/00* (2013.01); *Y10S 707/99941* (2013.01); *Y10S 128/92* (2013.01)
USPC ........... 600/300; 705/2; 705/3; 707/793; 707/999.1; 128/920

(58) Field of Classification Search
USPC ............ 600/300, 301; 128/903–905, 920
See application file for complete search history.

(56) References Cited

U.S. PATENT DOCUMENTS

| | | | | | |
|---|---|---|---|---|---|
| 5,950,630 | A | * | 9/1999 | Portwood et al. | 128/897 |
| 6,000,828 | A | * | 12/1999 | Leet | 705/2 |
| 6,113,540 | A | * | 9/2000 | Iliff | 600/300 |
| 6,283,761 | B1 | * | 9/2001 | Joao | 434/236 |
| 6,578,003 | B1 | * | 6/2003 | Camarda et al. | 705/3 |
| 7,319,970 | B1 | * | 1/2008 | Simone | 705/4 |
| 2002/0107452 | A1 | * | 8/2002 | Kwong | 600/509 |
| 2002/0123906 | A1 | * | 9/2002 | Goetzke et al. | 705/2 |
| 2002/0188476 | A1 | * | 12/2002 | Bienvenu et al. | 705/3 |
| 2003/0167189 | A1 | * | 9/2003 | Lutgen et al. | 705/3 |
| 2003/0212576 | A1 | * | 11/2003 | Kim | 705/2 |
| 2004/0143460 | A1 | * | 7/2004 | Marhaver | 705/2 |
| 2005/0137463 | A1 | | 6/2005 | Merkle | |
| 2008/0275731 | A1 | * | 11/2008 | Rao et al. | 705/3 |

FOREIGN PATENT DOCUMENTS

WO    01/69513    9/2001

OTHER PUBLICATIONS

NDC Directory, http://www.fda.gov/cder/ndc/; visited May 12, 2006.

(Continued)

*Primary Examiner* — Bill Thomson
*Assistant Examiner* — Marie Archer
(74) *Attorney, Agent, or Firm* — Steven A. Bern

(57) ABSTRACT

In general the invention is directed to systems, methods, and/or software modules which may analyze a patient's drug history, and optionally other data, and derive a probable diagnosis for the patient based on rules.

19 Claims, 5 Drawing Sheets

(56) References Cited

OTHER PUBLICATIONS

WHO Collaborating Centre for Drug Statistics Methodology, Norwegian Institute of Public Health, Oslo, Norway, http;//www.whocc.no/atcddd/.

International Classification of Disease schema, (available from the World Health Organization's website, http;//www3.who.int/icd/currentversion/fr-icd.htm, visited Jun. 6, 2006).

Fishman et. al.; "Risk Adjustment Using Automated Ambulatory Pharmacy Data: The RxRisk Model", Medical Care United States, vol. 41, No. 1, Jan. 1, 2003. pp. 84-99.

Zhao et al.; "Measuring Populations Health Risks using Inpatient Diagnoses and Outpatient Pharmacy Data", vol. 36, No. 6, Part II, Jan. 1, 2001, pp. 180-193.

* cited by examiner

MEDICAL DIAGNOSIS DERIVED FROM PATIENT DRUG HISTORY DATA

BACKGROUND

Systems and computer-implemented models are used to help predict costs for groups of patients, or find interesting patterns among patients having some common attribute or attributes. Resulting data may then be used to make decisions, or for further analysis. For example, cost prediction data may be used to estimate healthcare-related costs for a group of patients. Existing risk adjustment systems assign risk factors to individual patients, based on that patient's drug history. For example, if a given patient is taking both barbiturates and insulin, risk factors associated with both barbiturates and insulin would likely be assigned to the patient. The risk factors assigned to the patient comprise the patient's risk factor profile, and the profile may then be used to predict costs, based on past cost data from patients with similar risk profiles.

SUMMARY

Embodiments of the invention are generally directed toward deriving a medically relevant diagnosis for patient based on data associated with the patient. In certain embodiments, this data associated with the patient comprises such things as the patient's drug history, the patient's age, and the patient's sex. Other data associated with patient could also be used, such as genetic data describing the patient. Some embodiments of the invention apply rules to patient's drug history, alone or in combination with the patient's age, sex, or other associated information, and compute one or more diagnosis that is/are consistent with the patient's drug history and profile.

In one embodiment, the invention is directed to a computer-readable medium containing instructions operable to: receive patient profile data that at least identifies a patient's age and/or sex; receive drug history data that identifies at least one drug taken by the patient; evaluate the patient profile data, and the drug history data, in light of one or more drug diagnosis rules, the drug diagnosis rules defining relationships among or between data that comprises the drug history data or the drug diagnosis rules or the patient profile; and, assign a diagnosis to the patient based on the evaluation.

In another embodiment, the invention is directed to a system for determining a diagnosis for a patient based on at least the patient's drug history comprising: a database module containing: (1) the patient's profile data, the profile data including at least the age and sex of the patient, and (2) the patient's drug history, the drug history including information defining at least one drug the patient had previously received, and (3) a set of rules which define relationships between the patient's profile data and the patient's drug history, or relationships among information within the patient's drug history; a rules module, which evaluates rules held within the database module against information either in the patient's profile data, or the patient's drug history, or both; and a diagnosis assignment module, which assigns a probable medical diagnosis to the patient based on the rules module's evaluation.

In another embodiment, the invention is directed to, as part of a system which analyzes patients and assesses the patient's expected future demand for medical services or treatment, a software module which analyzes at least the patient's drug history and provides a diagnosis based on the patient's drug history.

In another embodiment, the invention is directed to a system for determining a patient's diagnosis based on, at least in part, the patient's drug history, the system comprising: means for receiving a patient's drug history, the drug history comprising at least one drug taken by the patient and a date or approximate date when taken by the patient; means for applying a rule or set of rules indicative of a disease to the patient's drug history, the rule or set of rules optionally additionally taking into account other patient attributes such as the patient's sex or age; means for, based at least in part on the application of the set of rules indicative of a disease, associating the patient with a diagnosis.

These and other embodiments of the invention are contemplated within this disclosure.

DETAILED DESCRIPTION

Figure 1:
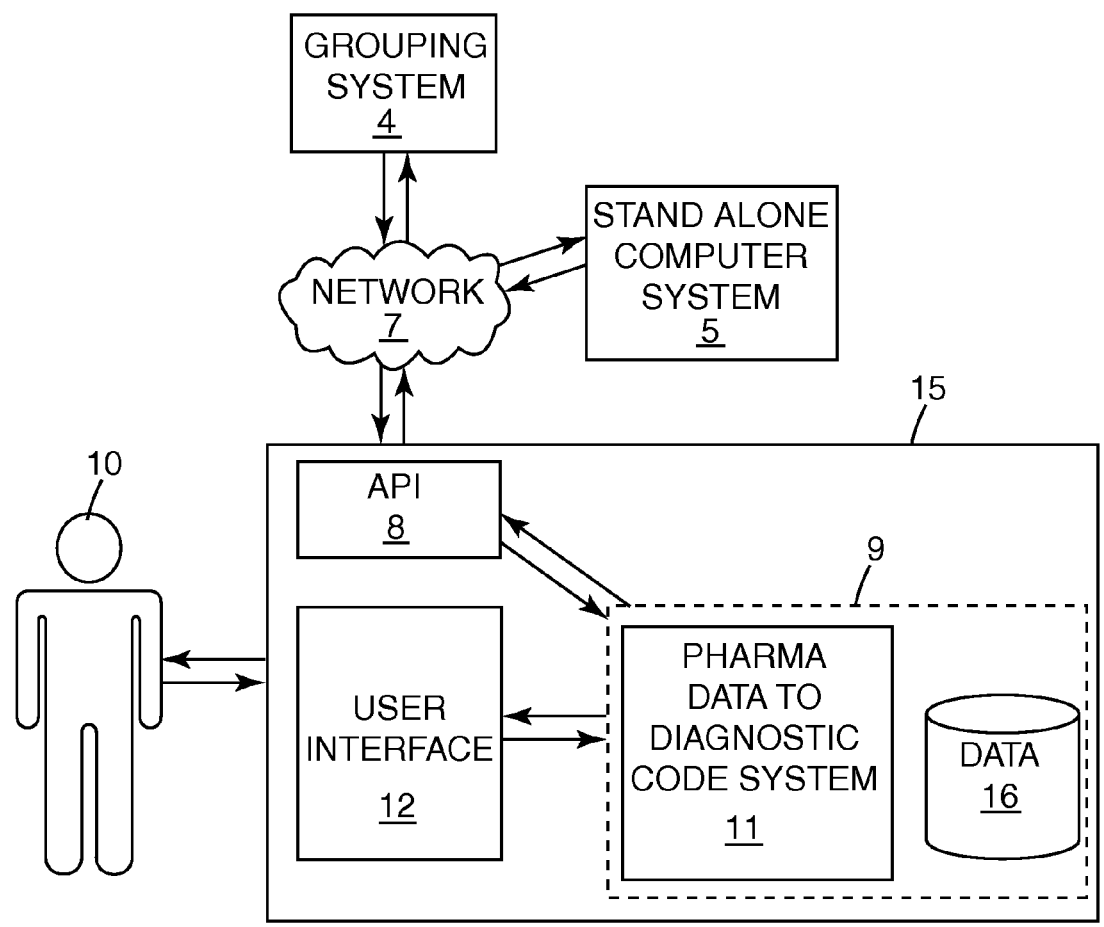
FIG. 1 is a diagram showing an exemplary embodiment of a prescription diagnosis system in the context of other infrastructure components.

FIG. 1 is a diagram showing an exemplary embodiment of prescription diagnosis system 9, which includes pharmaceutical data to diagnostic code system 11, and data 16. In certain embodiments, prescription diagnosis system 9 assigns or facilitates the assignment of a diagnosis to a patient based on the application of a set of rules to the patient's drug history and/or the patient's demographic record (age, sex, genetic factors, disease history, etc.). In certain embodiments this diagnosis can discern, for example, that a youth taking barbiturates likely has epilepsy, whereas an adult taking barbiturates in a certain pattern likely has migraine headaches. This information may be useful in ascertaining a more accurate prediction of the patient's risk and/or the expense of future patient treatment, or in analyzing data from many patients in search of interesting correlations between diagnosis and other data.

In one embodiment described herein, the prescription diagnosis system 9 is implemented in computing device 15, which may be any computer with a memory, such as a personal computer, a server, or a personal digital assistant. For exemplary purposes only, computing device 15 is shown further containing user interface 12 and application program interface (API) 8. Where such interfaces exist in a system's architecture, or whether they are required at all, is largely an implementation-specific consideration. Prescription diagnosis system 9 receives information defining a patient and at least a portion of the patient's prescription drug history and in one embodiment uses that data, and other data, to determine the patient's probable diagnosis or a procedure likely provided to a patient. A patient, as the term is used herein, is any person, and the term does not necessarily imply any particular relationship between the patient and another entity. These elements are referred to collectively as diagnosis data.

Information defining a patient is termed a demographic record. A demographic record in one embodiment contains a unique patient identifier and other information, such as the patient's sex, and the patient's date of birth. It may also contain metadata about the demographic record, such as a record type, which some applications may use to indicate the format and types of information that are included in a demographic record.

A patient's drug history is comprised of all drugs the patient is provided under the supervision of a physician or other medical health professional. A drug history is comprised of zero to many drug records. A drug record is data that defines a drug prescribed or administered to a patient, often by a medical doctor. If a patient has received multiple drugs, that patient would likely have a drug history containing a drug record for each of the drugs. Many of the drugs included in a patient's drug history are from prescriptions written by a qualified professional. As the term is used herein, a prescription is a controlled drug received by a patient, usually following advice by a qualified professional, such as a medical doctor. A drug record, in one embodiment, contains an indicator of drug code identification system, such as NDC or ATC, a drug code, the date of the prescription, and a patient identifier. NDC stands for National Drug Code; ATC stands for Anatomical Therapeutic Chemical. Both of these codes are described later in this description. The drug record in another embodiment simply identifies the pharmaceutical drug prescribed to the patient. The drug history or drug record may also contain metadata describing the type of history or record it is, and other useful information. A demographic record and its associated drug history are collectively referred to as patient data.

Figure 2:
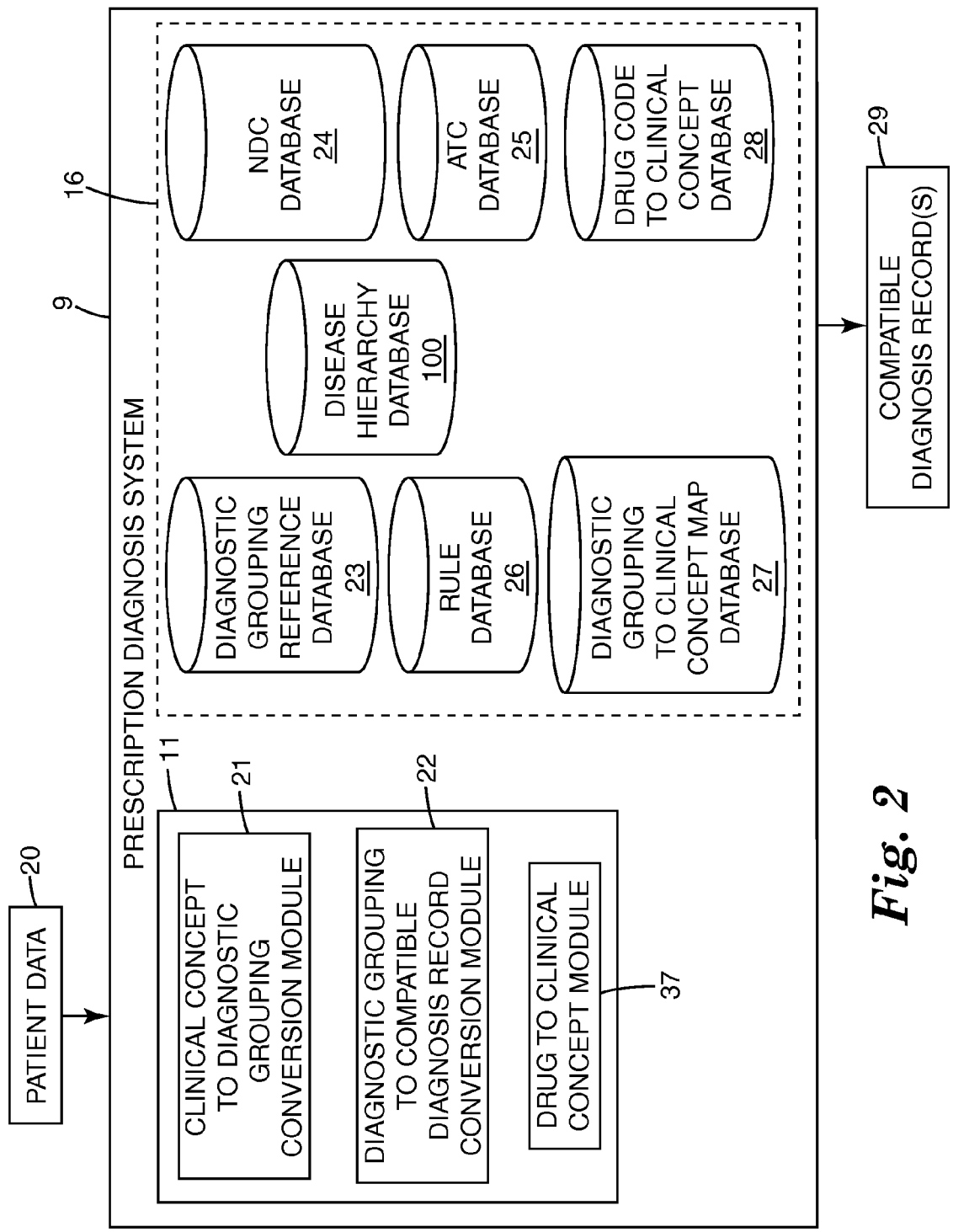
FIG. 2 is a diagram illustrating one example implementation of a prescription diagnosis system.

Prescription diagnosis system 9 is comprised of pharmaceutical data to diagnostic code system 11 and data 16. Prescription diagnosis system 9 may be implemented in a variety of ways, one or more exemplary manners of which are presented herein. Pharmaceutical data to diagnostic code system 11 in one embodiment contains functional modules that facilitate the analysis of a patient's drug history. One embodiment of certain functional modules of the pharmaceutical data to diagnostic code system 11 is shown in FIG. 2. Data 16 contains one or more databases that the functional modules of the pharmaceutical data to diagnostic code system 11 may use in its analysis of a patient's drug history. One embodiment is shown with respect to FIG. 2, which will be discussed further below. A user such as user 10 may remotely access prescription diagnosis system 9 via a client device, though various embodiments described herein focus on accessing and using prescription diagnosis system 9 via grouping system 4. For example, user interface 12 may be a web interface presented to a remote client device executing a web browser or other networking software. Data 16 may be implemented in a myriad of ways, as discussed further below.

Prescription diagnosis system 9 receives one or more demographic records and an associated drug history, in one embodiment via user interface 12. User interface 12 may be a graphical user interface which facilitates data entry or the selection of previously entered data from user 10. User 10 may be any person interested in accessing the functionality of prescription diagnosis system 9. User 10 may pay to access or use prescription diagnosis system 9, as would a managed care entity, which administers health insurance payments, or a case manager, or other persons or entity interested in overseeing a patient's case, or any other person or entity interested in using a disease classification system. Additionally, prescription diagnosis system 9 may receive information via API 8. API 8, among other things, allows other software systems or user interfaces to access functions of prescription diagnosis system 9. The API may or may not be implemented on the same physical system that contains prescription diagnosis system 9. In one embodiment, grouping system 4 accesses prescription diagnosis system 9 directly, without the use of user interface 12. Such access is more synonymous with batch record processing.

Network 7 may be any network, public or private, that carries information. In FIG. 1, network 7 connects computing device 15, and thus prescription diagnosis system 9, to stand alone computer system 5. User 10 may interact with stand alone computer system 5, for example, if user 10 is not in physical proximity to computing device 15. Network 7 also connects to grouping system 4. There are several grouping systems available commercially. Grouping systems are sometimes also referred to as risk adjustment systems, or risk classification systems. Grouping systems generally simplify a larger set of diagnostic codes into a more manageable subset. For example, a grouping system might break down the 14,000 or so disease or procedure codes used in the United States and specified in the International Classification of Disease (ICD) (which is available from the National Center for Health Statistics, via the United States Government's Center for Disease Control, and is currently in its ninth revision, and sixth volume), into about 500 or so sub-classifications (diagnosis codes) or 600 or so procedure code groups. The version of the ICD used in the United States is ICD version 9-Clinical Modification-Standard Usage. The particular IDC, or coding system, used is an implementation-specific detail largely irrelevant to the some embodiments of the invention. These sub-classifications are, for one grouping system 4 marketed by 3M of St. Paul, Minn., under the trade designation "3M CLINICAL RISK GROUPING SOFTWARE" referred to as Episode Diagnostic Codes (EDCs) or Episode Procedure Codes (EPCs). Grouping software such as 3M CLINICAL RISK GROUPING SOFTWARE may be used to determine, for example, one hundred or so diagnosis codes specified in the ICD are forms of the Episode Diagnostic Code associated with the diagnosis of gastric ulcers. 3M CLINICAL RISK GROUPING SOFTWARE uses demographic data, diagnosis codes, and procedure codes to identify and classify patients into clinically meaningful groups for risk adjustment and other purposes.

3M CLINICAL RISK GROUPING SOFTWARE is just one example of an embodiment of grouping system 4. Embodiments of prescription diagnosis system 9 may be coupled with or used with any grouping system, or risk classification system, produced by other manufacturers. In one embodiment, grouping system 4 makes automated calls through network 7 to API 8, providing a demographic record and associated drug history, and receives back diagnosis data.

Computing device 15 may read software instructions from a computer-readable medium (such as a hard drive, a CD-ROM, or a computer memory), or may receive instructions from another source logically connected to computer, such as another networked computer. Prescription diagnosis system 9 may be embodied in a computer-readable medium. Moreover, prescription diagnosis system 9 may be distributed to execute on multiple computers, and may be located remote to user 10 and accessible via a web browser or other interface.

FIG. 2 is a functional block diagram showing an exemplary implementation of prescription diagnosis system 9. Patient data 20 is shown as a data inflow. Compatible diagnosis record 29, which includes or comprises diagnosis data in suitable format, is an outflow. As shown in FIG. 2's exemplary embodiment, prescription diagnosis system 9 includes pharmaceutical data to diagnostic code system 11, which in turn contains three function modules. Functionality not attributed to any particular function module is attributed to the pharmaceutical data to diagnostic code system 11 generally, or the prescription diagnosis system 9 generally. Drug to clinical concept module 37 receives information defining a patient's drug history and returns a clinical concept. A clinical concept is a set of data, or criteria, which suggests one or more possible diagnosis, and is discussed further with respect to FIG. 3 and FIG. 4. Clinical concept to diagnostic grouping conversion module 21 takes the clinical concepts determined in the aforementioned drug to clinical concept module 37 and converts them, or associates them, with a diagnostic grouping. A diagnostic grouping is a grouping clinically similar diagnosis codes. For example, these groupings could be the same or similar groupings as provided by grouping system 4, discussed above. With respect to 3M CLINICAL RISK GROUPING SOFTWARE, the diagnostic and procedure groupings are the EDCs and EPCs. Diagnostic groupings can be as granular as necessary. Embodiments of prescription diagnosis system 9 can map to specific diseases as specified in the ICD. With respect to one embodiment described further herein, diagnostic groupings are at the EDC/EPC level to make the system more compatible with grouping system 4. Diagnosis grouping to compatible diagnosis record conversion module is explained more fully with respect to FIG. 3 and FIG. 5. Finally, diagnostic grouping to compatible diagnosis record conversion module 22 receives the diagnostic grouping data produced in the aforementioned module and provides a record, or string, in a format and manner compatible with whatever system, function, user, or otherwise, requesting the analysis of prescription diagnosis system 9. Diagnostic grouping to compatible diagnosis record conversion module 22 is described more fully with respect to FIG. 3 and FIG. 6.

FIG. 2 includes an exemplary implementation of data 16, which in this embodiment contains six databases. A database is a collection of information which may be accessed by a computer. Data 16, and its constituent databases, may be implemented in a variety of forms including data storage files, computer memory, or one or more database management systems (DBMS) executing on one or more database servers. The database management system may be a relational (RDBMS), hierarchical (HDBMS), multidimensional (MDBMS), object oriented (ODBMS or OODBMS) or object relational (ORDBMS) database management system. Data 16 could, for example, be stored within a single relational database such as SQL Server from Microsoft Corporation. In one embodiment, data 16 is a flat file loaded into memory of computing device 12. In another embodiment, data 16's constituent databases are spreadsheets in a form compatible with a product marketed by Microsoft Corporation of Redmond, Wash., under the trade designation "EXCEL."

National Drug Code (NDC) Database 24 contains all prescription drugs or insulin manufactured, prepared, propagated, compounded, or processed for commercial distribution in the United States. The NDC is an industry standard product identifier. It is comprised of a unique, three-segment number. The Food and Drug Administration makes available on its website the NDC directory, which may be used to look up active ingredients using a portion of the NDC identifier. NDC database 21 contains an implementation of the NDC directory such that an NDC number, which identifies a pharmaceutical product, can be de-referenced against a listing of active ingredients. More information about the NDC Directory is available at the website address http://www.fda.gov/cder/ndc/, which was visited May 12, 2006. The industry standard NDC code is an 11 character number. The last two characters are packaging codes, which are not relevant to prescription diagnosis system 9. Thus, in one embodiment, NDC database 24 identifies drugs by the 9 digit NDC number only, and active ingredients for a given drug may be found using the 9 digit truncated NDC number. NDC database 24 also includes a mode of administration, which is also available from the FDA at the above-mentioned website (as of May 12, 2006). The information regarding modes of administration is merged into the table that becomes NDC database 24. An example entry in the NDC database 24 is as follows: 000850614|ALBUTEROL|PROVENTIL INHALATION AEROSOL|january 2006 The first field is the 9 digit NDC code, the second field is the active ingredient, the third field is the a commercial name of the drug, and the final field is the last date the entry was a part of the FDA data upon which the NDC database 24 is compiled. An NDC code may have multiple entries if it has multiple active ingredients. Some ingredients that are known to be insignificant (considering or not considering route of administration) from a diagnosis standpoint may be excluded from NDC database 24, but this exclusion is not necessary. Other drugs or classes of drugs may be similarly excluded from NDC database if they treat minor ailments of little interest to the users of the system (an example of such drugs might be those used to treat minor skin rashes, some of which are diagnosed as eczema), If the route of administration for an NDC entry is diagnostically significant, the name of the active ingredient is modified to signify such. For example, TIMOLOL MALEATE, a common beta blocker, treats different diseases taken orally or via a drop to the eye ball. The NDC row associated with TIMOLOL MALEATE in tablet form is as described above. However, the NDC row associated with TIMOLOL MALEATE in dropper form is modified such that the active ingredient is GL_TIMOLOL MALEATE, the "GL_" being added to signify the alternative disease indicated by the route of administration (in this case, glaucoma).

ATC Database 25 contains the Anatomical Therapeutic Chemical (ATC) codes of the World Health Organization. ATCs classify therapeutic drugs into different groups according to the organ or system on which they act and their chemical, pharmacological and therapeutic properties. ATCs are maintained by, and available from, the WHO Collaborating Centre for Drug Statistics Methodology, Norwegian Institute of Public Health, Oslo, Norway. An ATC is a unique 7-digit alpha-numeric code, which identifies the active ingredient itself. ATC database 25 contains the ATC codes and the name of the corresponding active ingredient or ingredients. ATC database 25 is created and formatted similarly to NDC database 24.

Drug code to clinical concept database 28 contains a subset of drugs that have a corresponding clinical concept. A clinical concept is the name of the third field of the drug code to clinical concept database 28, and contains a series of ones and zeros indicating one or more active ingredients, modified active ingredients, or drug groups the drug code is associated with, as described below. Drugs not having a clinical concept in one embodiment are excluded from the clinical concept database 28. Drug code to clinical concept database 28, in one embodiment, has the following fields:

Drug Code Type, which indicates if the record is of type NDC, ATC, or otherwise.

Drug Code, which is the modified NDC code (9 characters; last two characters of original 11 characters eliminated), or ATC code, or whatever is implicated in Drug Code Type field.

Clinical concept, which is a string of zeros and ones, (0=false, 1=true) corresponding to particular active ingredient, modified active ingredient group, or drug classes. Active ingredients are pulled from the NDC database 24 and/or ATC database 25, or a database similarly populated with data available from the US Food and Drug Administration, or other sources, public and private. Modified active ingredients are active ingredients wherein the route of administration is deemed of diagnostic interest. Modified active ingredients, in one embodiment described above, are already part of NDC database 24. For example, there exist several dozen beta blockers, such as TIMOLOL, used to treat a cardiovascular condition when taken orally. However, these drugs may be taken in liquid form, via a dropper to the eye ball, to treat glaucoma. TIMOLOL, then, is both an active ingredient, as well as a modified active ingredient. TIMOLOL in non-droplet form also happens to be a member of a drug class, in this case one defined as "beta blocker." Drug classes are groups of drugs for which, from a diagnostic viewpoint, the constituent drugs are clinically comparable. In one embodiment there are several dozen drug classes or more. For example, there are many active ingredients in the "beta blocker" drug class. Within a particular time period, if a user switches between one active ingredient in the beta blocker drug class and another, this switch, in some instances, may not be significant and likely indicative only of different attempts to treat the same underlying disease. In other words, the reasons for the switch between beta blockers is not known, but the underlying disease likely has not changed. The drug class data construct is a mechanism to identify those active ingredients or modified active ingredients that have clinically similar applications. Determining the listing of modified active ingredients, as well as defining drug classes (comprised in one embodiment of active ingredients and modified active ingredients), is an implementation-specific matter, which may be addressed in myriad ways, or not addressed at all.

As mentioned, each row in drug code to clinical concept database 28 represents a drug for which there is a corresponding active ingredient, modified active ingredient, or drug class. Excluded from drug code to clinical concept database 28 are drugs for which the active ingredient is not indicative of a specific medical diagnosis. For example, purified water, denatured alcohol, glycerin, fillers, dyes, or acetaminophen might be excluded from drug code to clinical concept database 28.

A simplified exemplary entry in drug code to clinical concept database 28 might be represented as follows:
1 000023251 00000001010000000000100000 . . . .

The second field of the first row, 000023251, might correspond, for example, to a particular type of insulin; for the purposes of this example we will call it BRANDX INSULIN. The first "1" in the third field may indicate, in this example, that BRANDX INSULIN is associated with the active ingredient INSULIN RECOMBINANT HUMAN. The second 1 may indicate BRANDX INSULIN is a member of the drug class "insulins." In other words, for the purposes of a later diagnosis of the patient by prescription diagnosis system 9, the particular type of insulin may be irrelevant; all that may matter is the associated drug class, which in this example is "insulins." Subsequent 1s in the third field indicate that BRANDX INSULIN also includes other active ingredients, and may be associated with other drug classes.

Drug code to clinical concept database 28 is, in one embodiment, generated and maintained in the following manner, though one skilled in the art will recognize a myriad of other ways similar maintenance could be achieved. A spreadsheet is maintained having, in rows, all active ingredients, as from public listings described above, as well as modified active ingredients, defined internally. Columns in the spreadsheet correspond to drug classes. The intersection of a column and a row may contain a digit or be blank. If the intersection contains a digit, this is indicative of the active ingredient or modified active ingredient being associated with a corresponding drug class defined by the columns. In one embodiment, there is an additional "delete" column designating those rows for which there is no corresponding drug class, or for which the drug is not diagnostically significant. Rows marked as delete may be purged or not further processed at a later time. There may be further columns associated with special drug classes, such as those drug classes associated with a type of disease flagged for special processing. One such drug class may be chemotherapy drugs, which in one exemplary implementation, are flagged as special because they have both an associated disease code (one associated with the malignancy) and a procedure code (associated with the treatment). The selection of what columns to setup and how to setup this table is implementation-specific, depending on a number of factors. In summary, however, there may be additional columns setup and defined to have special meaning, or indicate special processing of a drug.

An internal data structure, hash table, or database may then be generated by combining all active ingredients and modified active ingredients where there is no entry in the "delete" column, and additionally includes all drug classes from the columns. These are then sorted alphabetically. The ones and zeros of the third field of drug code to clinical concept database 28 correspond to this alphabetically organized internal data structure, hash table, or database. One skilled in the art will recognize there are many other ways to implement the same notion of keeping track of drugs and their associated active ingredients, modified active ingredients, and/or drug classes. Herein described is one such manner, but this and others are within the scope of the invention.

Rule database 26 contains a set of conditions, or rules, based on demographics and patterns of occurrence. A rule might define, for example, that if a person is of a particular age and sex, a particular condition might apply depending on the administered drug, and possibly other factors related to the drug's administration, such as the length or pattern of administration. Rule database 26, in one embodiment, includes a primary key rule number, a description of the rule, a number indicating the number of occurrences required to meet the rule, a number indicating the number of different days for which the occurrence must be reported or be present to meet the rule, a number indicating the number of spans required to meet the rule, a number indicating the number of days a span must be to meet the rule (span length), a number indicating the number of breaks required to satisfy the rule (a break is a period in which diagnostic grouping data is not reported or available), a number indicating the number of days the breaks must be to satisfy the rule, an indication of the patient's sex required to meet the rule, an indication of the patient's minimum age required to meet the rule (in both days and years), an indication of the patient's oldest age required to meet the rule (in both days and years). The break data may not be used in subsequent computing, and is provided for compatibility purposes. An exemplary row is as follows:

Rule number: 27
Description: Age 18-34
Number of occurrences to meet the rule: 1
Number of different days the occurrence must be reported: 365
Spans: 0
Span length: 0
Break number: 0
Break length, days: 0
Break length, years: 0
Sex: 0
Age youngest: 18
Age oldest: 34
Age youngest in days: −1
Age oldest in days: −1

A zero for sex indicates the rule is sex neutral. A "1" indicates the rule applies only to a female, and a "2" indicates the rule only applies to a male. A "−1" in age youngest and oldest in days signifies the field is not used. Zeros in the spans and breaks means there is no associated span or break rule. One skilled in the art will recognize that the rules presented herein are merely a small subset of the possible rules that could be used to further refine diagnosis based on a patient's drug history. Other factors taken into account by a rule may include the patient's disease history or genetic characteristics, which may include genetic attributes associated with the patient and statistically indicative (positively or negatively) with a diagnosis.

Diagnostic grouping to clinical concept map 27 is used by prescription diagnosis system 9 to assign diagnosis grouping codes to a patient. At a high level, diagnostic grouping to clinical concept 27 consists of criteria which, if satisfied, will result in the assignment of a diagnostic grouping. Diagnostic grouping to clinical concept map 27 also identifies rules that must be evaluated to "true" in order for a diagnostic grouping to apply. Each row in diagnostic grouping to clinical concept map 27 comprises a clinical concept rule specification, and contains, in one example embodiment, the following fields:

Diagnostic Grouping Indicator, specifies whether the record is related to a disease or a procedure, 1 being disease, 2 being a procedure.

Diagnostic Grouping Number, specifies diagnostic groups. For example, 3M CLINICAL RISK GROUPING SOFTWARE has, as an episode diagnostic code, or EPC, a particular type of epilepsy identified by the EDC as "Epilepsy-Intractable." This particular EDC has a key of "23." Thus, the diagnostic grouping number would be 23.

Diagnostic Group Description, specifies the name of the diagnostic group.

Continuing the example introduced above with respect to epilepsy, the field would read "Epilepsy-Intractable."

Clinical Concept #1, specifies an active ingredient, modified active ingredient, or drug class associated with the diagnostic group. The possible active ingredients, modified active ingredients, and drug classes are, in one embodiment, the same as described with respect to the clinical concept field of drug code to clinical concept database 28, described above.

Clinical Concept #1 Rule, specifies the associated rule number, which may be de-referenced in rule database 26.

Clinical Concept #2, specifies a further active ingredient, modified active ingredient, or drug class, like Clinical Concept #1.

Clinical Concept #2 Rule, specifies the associated rule number, which may be de-referenced in rule database 26.

Clinical Concept #3, specifies a further active ingredient, modified active ingredient, or drug class, like Clinical Concept #1.

Clinical Concept #3 Rule, specifies the associated rule number, which may be de-referenced in rule database 26.

Each record in diagnostic grouping to clinical concept map 27 has at least one clinical concept, and in the embodiment described herein, may have an additional one or two clinical concepts. As will be seen, in one embodiment, all rules associated with all of the three clinical concepts must evaluates to "true" in order to result in a determination that the diagnostic grouping applies to the patient. Any number of further clinical concepts could be specified, on an implementation-specific basis. Diagnostic grouping to clinical concept map 27 may have a record for each diagnostic grouping that has a drug history profile. Further, there may be many different drug history profiles that suggest a diagnostic grouping, so a particular diagnostic grouping may often have many entries within diagnostic grouping to clinical concept map 27.

Disease hierarchy database 100 includes information defining the order in which diseases should be assigned. For example, a particular drug usage pattern in a patient's drug history may implicate more than one disease. Prescription diagnosis system 9 uses the disease hierarchy database 100 to ensure the more severe of the possible diagnosis is the one that is actually assigned. In this way, ambiguities resulting from interpretation of a patient's drug history are resolved in favor of more severe, rather than less severe, disease.

Disease hierarchy database 100 includes, in one embodiment, two tables. The first table, MDC hierarchy table, specifies the hierarchy of MDCs. MDC stands for Major Disease Category. An MDC is a very broad classification of disease. MDCs may correspond to a single organ system or disease etiology. Malignancies and multiple trauma may be assigned their own MDCs. Diseases that include both a particular organ system and a particular etiology (e.g., urinary tract infection) are assigned to an MDC corresponding to the organ system involved. Systemic infectious diseases (e.g., septicemia) are also grouped into a distinct MDC. Another set of the MDCs consist of diagnostic groups related to catastrophic conditions, bone marrow transplants, and malignancies. The definition of which diagnostic groups, and in turn which diseases, comprise an MDC is an implementation-specific decision. Examples of MDCs include "CATASTROPHIC RESPIRATORY CONDITIONS", or "MALIGNANCIES."

EDCs, or Episode Diagnostic Codes (also referred to generically as diagnostic groups), or EPCs (Episode Procedure Codes) define diseases or procedures at a more granular level. Whereas there are about 40 or so MDCs, there are several hundred EDCs and EPCs. EDCs and EPCs are associated with an MDC.

MDC hierarchy table (one of the tables in disease hierarchy database 100), in one embodiment, includes one record for each MDC, each record containing three fields as follows:

MDC Number, which is a primary key unique to the MDC.

Rank, which specifies the order in which MDCs should be evaluated, and thus assigned.

Description, which is a description of MDC.

Disease hierarchy database 100 also includes, in one embodiment, a second table called diagnostic group hierarchy table. The table contains, for each MDC, a ranking of diagnostic groups within the MDC. The table has three columns, as follows:

Diagnostic Group Number, which is a unique number associated with a diagnostic group.

MDC Number, which is the associated MDC number as described above with respect to the MDC hierarchy table.

Diagnostic Group Rank, which is a number between 1 and the total number of diagnostic groups contained within an MDC.

Figure 3:
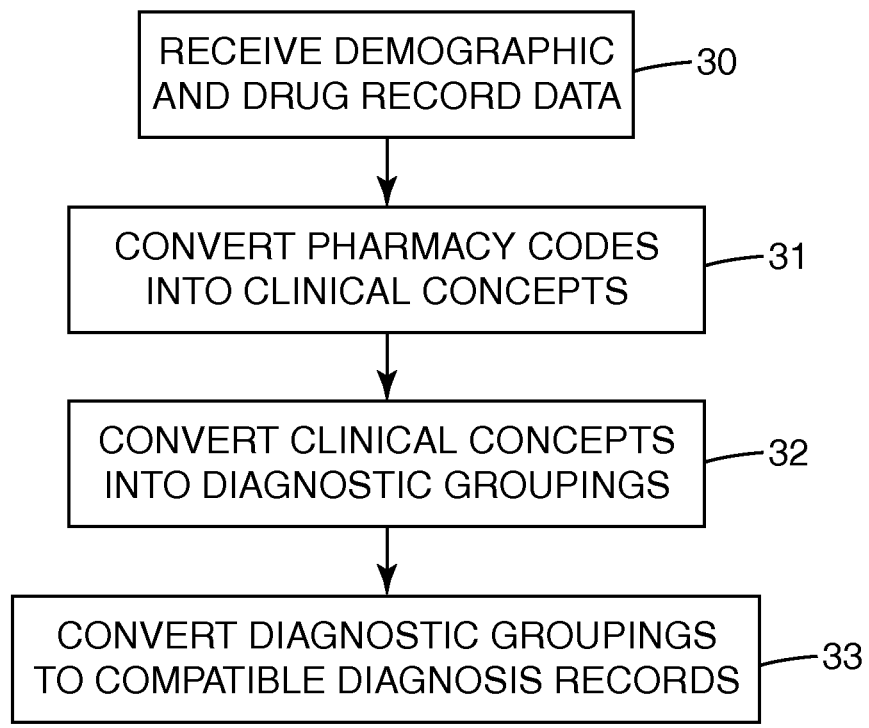
FIGS. 3, 4, and 5 are flowcharts diagrammatically illustrating parts of an exemplary process whereby a diagnosis is determined for a patient.

Diagnostic grouping reference database 23 contains information linking data structures defining diseases which are used within prescription diagnosis system 9 to an output compatible with the system, person, or API calling prescription diagnosis system 9 to determine a diagnosis. In one embodiment, diagnostic grouping reference database 23 contains diagnostic group numbers and MDC numbers, which may be used to look up the diagnostic group description, or the description as specified in the ICD. Exactly what data is to be looked up and returned from this database is an implementation specific detail. Diagnostic grouping reference database 23 may be helpful in integrating prescription diagnosis system 9 into existing infrastructures that use different, tailored, or semi-tailored diagnostic grouping schemas. In one embodiment, the diagnostic group name and the ICD description and associated key, may be de-referenced and returned from diagnostic grouping reference database 23. An example entry in diagnostic grouping reference database may be as follows:

"5": Indicates the EDC or EPC key number
"1": Whether EDC/EPC number is an EDC or EPC key
"Neurodegenerative Diagnoses Except Multiple Sclerosis and Parkinson's": Diagnostic group name
"CEREBRAL LIPIDOSES": ICD version 9-CM name FIG. 3 is a flowchart showing an exemplary high-level flow of one manner in which prescription diagnosis system 9 may receive patient data, analyze it, sometimes in light of other data, and produce diagnosis data likely relevant to the patient's condition. First, prescription diagnosis system 9 receives demographic and drug record data (30). This data may include, for example, a patient's demographic record, as well as a patient's drug history, which may be comprised of one or more drug records. A patient's demographic record and drug history, the two constituent pieces of data received in this initial step in this embodiment, are referred to as patient data. The specific constituents of the patient data described herein are for exemplary purposes only; one skilled in the art will recognize many permutations of the data requirements necessary to enable this and other embodiments of the invention.

Next, pharmacy codes are converted into clinical concepts (31). This step is, in substantial part, and in one embodiment, functionally encompassed by drug to clinical concept module 37, which may be seen with respect to FIG. 2. Like other details about the implementation, however, the specifics of how the prescription diagnosis system 9 may be implemented, and particularly what functionality may reside in what module, are immaterial to the concepts described herein. At a high level, a patient's drug history is analyzed and cross-referenced with other databases, which produces pharmacy codes. Pharmacy codes are then assigned a clinical concept. This process if further detailed with respect to FIG. 4.

Clinical concepts are then converted into diagnostic groupings (32). Clinical concepts are, in one embodiment, comprised of relatively granular data, because the clinical concepts in one embodiment are described using the International Classification of Disease schema, (available from the World Health Organization's website, http://www3.who.int/icd/currentversion/fr-icd.htm, visited Jun. 6, 2006). The ICD contains roughly 14,000 codes, each defining a clinical diagnosis. There are several commercially available products that group these thousands of ICD codes into a more manageable superset of clinical diagnosis. These products, as mentioned above, are generally referred to as risk adjusters.

For exemplary purposes, portions of 3M's risk adjustment software is described. 3M CLINICAL RISK GROUPING SOFTWARE defines 534 EDCs (as well as EPCs), each assigned to an MDC (discussed above).

This step is, in part, and in one embodiment, functionally encompassed in clinical concept to diagnostic grouping conversion module 21, which may be seen with respect to FIG. 2. A more particular exemplary implementation of this step may be seen with respect to FIG. 5.

Finally, the diagnostic groupings are converted into compatible diagnosis records (33). This step may not be necessary if the diagnostic grouping data, as is, is already acceptable. In one embodiment, this step formats the data in a manner such that it will be compatible with grouping system 4. In another embodiment, the data is formatted and/or combined with other data to make suitable for some other use, user, application, or calling function. In another embodiment, the diagnostic groupings are not converted to a different record type and are instead returned in their native format. Conversion of diagnostic groupings to compatible diagnosis records is, in part, and in one embodiment, functionally encompassed in diagnostic grouping to compatible diagnosis record conversion module 22, which may be viewed in one embodiment with respect to FIG. 2. A more particular exemplary implementation of this step may be viewed with respect to FIG. 6.

At a high level, then, a patient's drug history is received by the prescription diagnosis system, and some type of indication of a probable diagnosis is returned by the system. As will be recognized and appreciated by one skilled in the art, there are many alterations and permutations on the steps necessary or useful to start with the data so indicated, and arrive at a probable diagnosis for the patient. These and other embodiments are contemplated within the scope of the invention.

Figure 4:
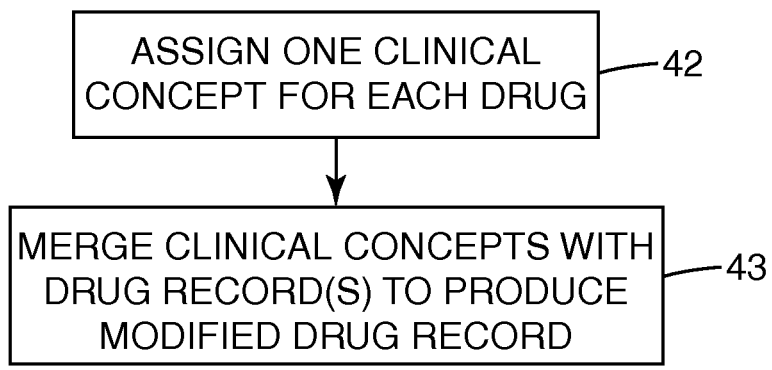

FIG. 4 is a flowchart showing an example manner in which drug codes included in a patient's drug records are converted into clinical concepts, as referred to earlier with respect to exhibit 31 of FIG. 3. The conversion is, in one embodiment, the function of drug to clinical concept module 37.

In the sub-process described with respect to FIG. 4, each drug record in a patient's drug history is, in one exemplary embodiment, either eliminated from consideration or linked to a clinical concept, which is then passed on for further analysis. For each drug in a patient's drug history, drug to clinical concept module 37 assigns a clinical concept, if one is exists (42). This is done by looking the active ingredient code up in drug code to clinical concept database 28. Active ingredients not found in code to clinical concept database are discarded. As mentioned earlier, there are several reasons why a clinical concept may not exist for every drug.

Once a drug present in the clinical concept database and present in the patient's drug history have been associated, the resulting record is called the modified drug record (43). The modified drug record contains the drug record plus, where applicable, associated clinical concepts. The patient's drug history is, in one embodiment, updated with information contained in the modified drug record. At this point in the process, the patient's drug history contains drug records and modified drug records. The drug records are drugs for which there was not yet an associated clinical concept. The modified drug records are the drugs for which a clinical concept has been assigned. The modified drug record, in one embodiment, is structured similarly to a drug record, except it contains an additional field of digits corresponding to the last field in the code to clinical concept database 24.

Figure 5:
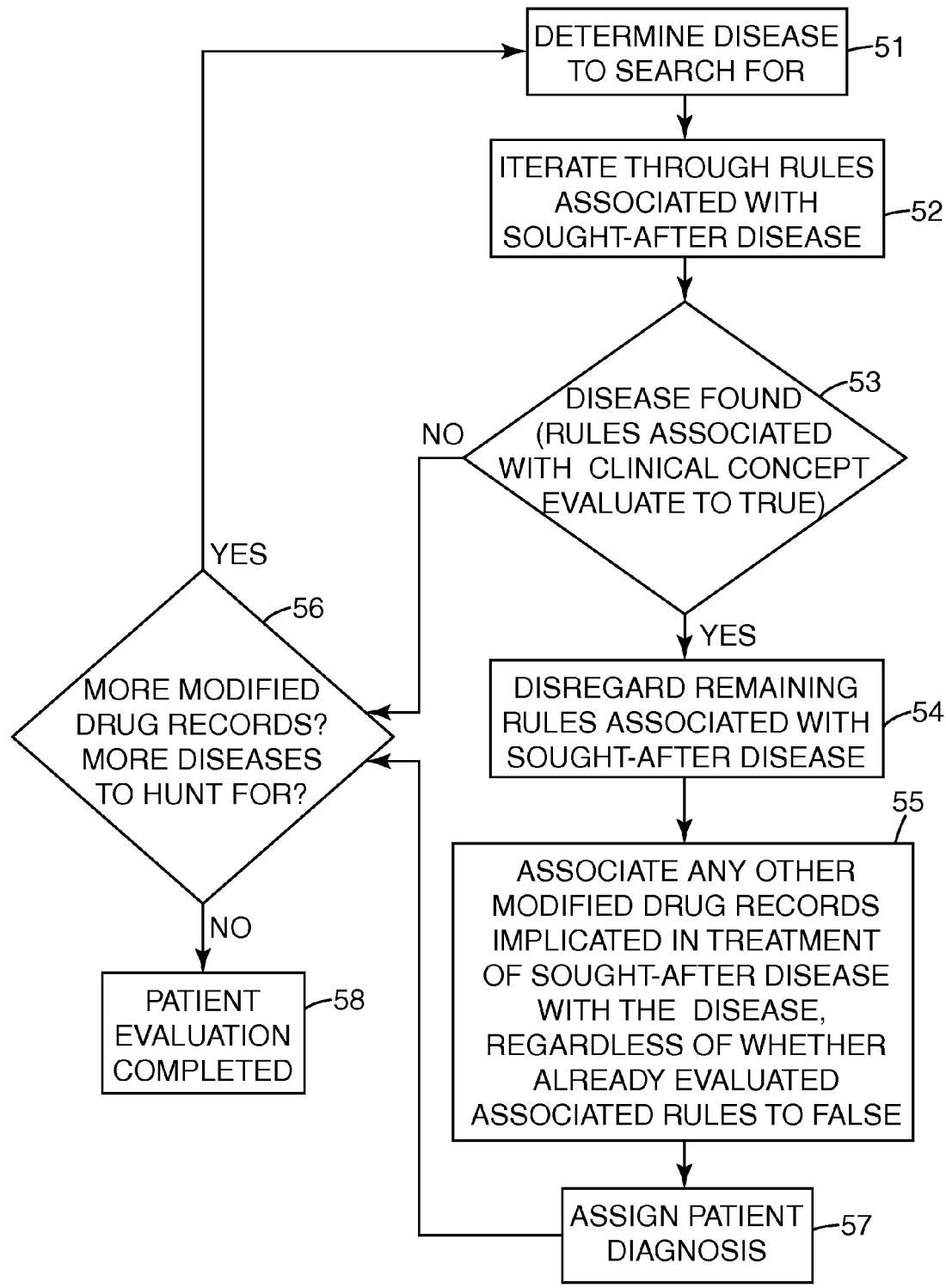

FIG. 5 is a flowchart showing an example manner in which clinical concepts are converted into diagnostic groupings which imply a diagnosis, as referred to earlier with respect to exhibit 32 of FIG. 3. The conversion is, in one embodiment, the function of clinical concept to diagnostic grouping conversion module 21.

First, clinical concept to diagnostic grouping conversion module 21 determines which disease to hut for first (51). This is accomplished, in one embodiment, via a lookup in the disease hierarchy database 100. More severe diseases are searched for first, as the prescription diagnosis system is designed, in some embodiments, to resolve ambiguities in favor of associating a patient with the most severe disease supported by the patient's drug record, as will be seen. A first modified drug record is selected from the patient's drug history. In the embodiment described herein, the order in which the patient's drug history is processed is not relevant as it does not have bearing on the ultimate diagnosis assigned to a patient.

Next, prescription diagnosis system 9 iterates through all rules, or criteria, associated with the sought-after disease (52). This application of the rules, in one embodiment, may be done as follows: First, prescription diagnosis system 9 determines which drugs or drug classes are associated with treatment of the sought-after disease. This may be done by first determining the drug's active ingredient, modified active ingredient, or drug class via a lookup information contained in one or more databases, such as drug code to clinical concept database 28 and/or diagnostic grouping to clinical concept map database 27. Particularly, the first active ingredient, modified active ingredient, or drug class indicated within the modified drug record's clinical concept field (the first "1") is looked up in diagnostic grouping to clinical concept map 27, clinical concept #1 field (52). The associated rule is then looked up in rule database 26, and compared against the patient's drug history. If the patient's drug history is consistent with the rule, the subsequent clinical concepts (up to two more, in one embodiment as described above) are evaluated by prescription diagnosis system 9. If there is a second or third clinical concept listed in the diagnostic grouping to clinical concept map 27 record, the associated rule, in one embodiment, must evaluate to "true" also. In this manner, each active ingredient, modified active ingredient, or drug class associated with a prescription drug must have one, two, or three rule sets evaluate to "true" in order for the associated diagnostic grouping to apply to the prescription drug. If any of the one, two, or three rule sets evaluate to "false", the clinical concept is eliminated from further consideration and the iteration through rules and clinical concepts associated with the disease continues. As part of this continued iteration, clinical concept to diagnostic grouping conversion module determines whether there are further entries within diagnostic grouping to clinical concept map 27 that are implicated in treating the sought-after disease (have the same active ingredient, modified active ingredient, or drug class). If there are, these are evaluated in the same manner as described.

Through this iteration, in applying rules related to a disease to a patient's drug history, either a rule will evaluate to "true" or "false" for a given disease (53). If no rules evaluate to true, prescription to diagnosis system 9 determines if there are more modified drug records in the patient's drug history, or if there are further, less severe diseases to hunt for (56). If both of these conditions are true, the iterative process just described continues on the next disease, and in turn modified drug record. If either of these conditions is false, then the prescription diagnosis system is finished with the patient's drug history evaluation.

If a rule for a sought-after disease evaluates to "true" ("true" at 53), prescription diagnosis system 9 ignores, or marks as processed, all other drugs in the patient's drug history associated with the treatment the illness that have not been evaluated (54). In other embodiments, the remaining rules may still be evaluated, but this step is not necessary. Further, all modified drug records already evaluated as being implicated in the treatment of the sought-after disease which evaluated to false are assigned to the diagnosis so they will not be further assessed in the hunt for lesser diseases (55). These two steps, taken together, set up a bias toward implicating as many modified drug records as possible in the treatment of the most serious disease implicated by the patient's diagnosis. In so doing, the two rules reduce false positive diagnosis, and help address issues surrounding the nature of a patient's drug history when that patient is, for example, in a phase of treatment where a doctor is trying different approaches to test which ones may elicit a better patient response, but as such do not meet rules defining model drug histories for the patient. The diagnosis is then assigned, in the computer memory, to a patient (57), and a check is done as to whether there are further modified drug records, and whether there are remaining diseases to hunt for. If either inquiry evaluates to false, the evaluation of the patient's history by prescription diagnosis system 9 is completed (58), the assigned diagnosis saved to computer memory (or some other means of storage), ready for further processing if so desired per the implementation.

The process continues until all sought-after diseases have been processed or there are no further unassigned modified drug records.

Figure 6:
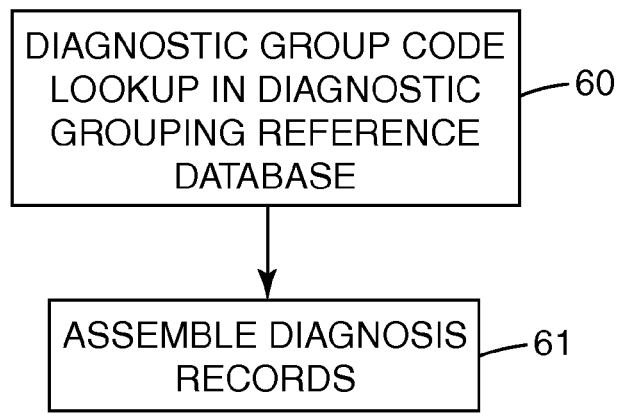
FIG. 6 is a flowchart illustrating the assembly of diagnosis records after the previously determined diagnosis is de-referenced against another data set.

FIG. 6 is a flowchart showing an example manner in which diagnostic groupings are converted into a system-compatible format, as referred to earlier with respect to exhibit 33 of FIG. 3. The conversion is, in one embodiment, the function of diagnostic grouping to compatible diagnosis record conversion module 22. This step serves to correctly prepare the data for subsequent receipt by a calling function, calling application, user, or otherwise. As such, it may not be required, and its implementation, like that of other modules and information flows described herein, is an implementation-specific detail. The example set forth with respect to FIG. 6 first looks up diagnostic grouping numbers in the diagnostic grouping reference database 23 (60) to retrieve the ICD disease names and numbers, and/or the diagnostic grouping names and numbers. Diagnostic grouping to compatible diagnostic record conversion module 22 then, in one embodiment, assembles a string of proper length and formatting such to be compatible with grouping system 4, and assembles one or more of these strings, line by line, into a file (61), which may be returned to user 10, the calling program, the calling function, or otherwise.

Figure 7:
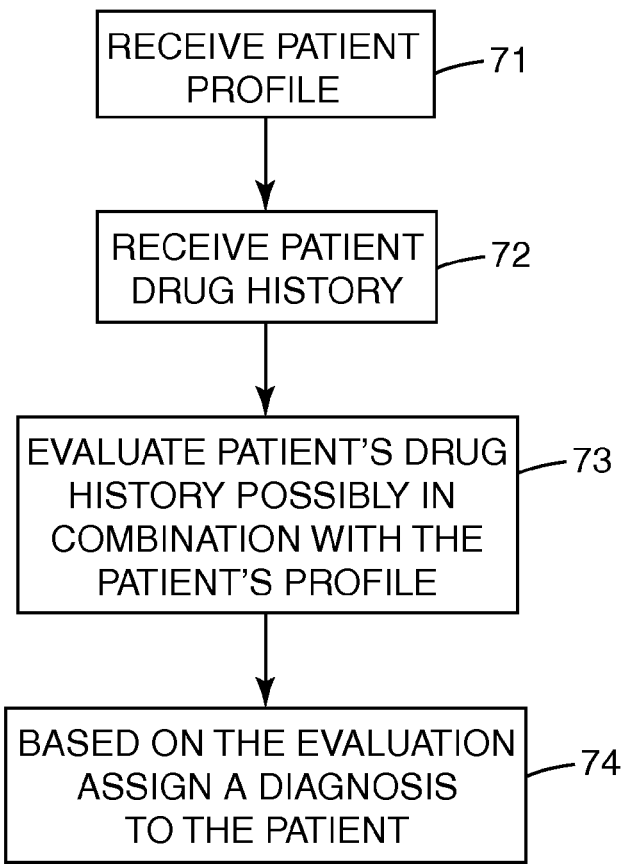
FIG. 7 is a flowchart diagrammatically showing a high level process flowchart.

FIG. 7 is a flowchart diagrammatically illustrating a high-level exemplary process, a particular implementation or embodiment of which is described in the preceding text. First, and in summary, a patient profile is received by the prescription diagnosis system 9 (71). Next, the patient's drug history is received (72). Then the patient's drug history is evaluated, possibly in light of various factors in the patient's profile (such as age, sex, genetic factors, or disease history), using sets of rules associated with a sought-after disease (73). Finally, based on the evaluation, a disease is assigned to the patient (74).

The invention claimed is:

1. A non-transitory computer-readable medium having computer-executable instructions operable to cause a computer to;
   receive patient data indicative of a patient's age and sex;
      receive drug history data that identities drugs taken by the patient;
      apply one or more drug diagnosis rules to the patient data and the drug history data, the drug diagnosis rules defining relationships between drug history data, the patient's sex, the patient's age, and a diagnosis; and,
      infer the diagnosis for the patient based on the application of the one or more drug diagnosis rules.

2. The computer-readable medium of claim 1, wherein the drug history data includes information additionally defining time periods in which a drug was taken or received by a patient.

3. The computer-readable medium of claim 2, wherein the drug diagnosis rule includes a span rule, which defines a period of time for which the patient must have been taking a drug for a diagnosis to apply.

4. The computer-readable medium of claim 3, wherein the span rule includes gap rules, which define gaps in the period of time for which a patient must have been taking a drug for a diagnosis to apply.

5. The computer-readable medium of claim 1, wherein the drug diagnosis rules include an age rule, which defines the age of the patient at or near the time a drug was taken in order for a diagnosis to apply.

6. The computer-readable medium of claim 1, wherein the drug diagnosis rules include a sex rule, which defines the sex of the patient at the time a drug was taken in order for a diagnosis to apply.

7. The computer-readable medium of claim 1, wherein assigning a diagnosis to the patient comprises:
   receiving a diagnosis hierarchy defining a plurality of possible diagnoses, the hierarchy a function of either disease severity or cost of treatment, or some combination thereof;
   assigning the diagnosis to the patient based on selecting the highest diagnosis in the hierarchy that is consistent with the drug diagnosis rules in instances where there exists more than one diagnosis that is consistent with the drug diagnosis rules.

8. The computer-readable medium of claim 1, wherein the drug history data identifies more than one drug taken by the patient, and wherein applying the drug diagnosis rules further comprises applying the drug diagnosis rules to the second drug taken by the patient.

9. The computer-readable medium of claim 1, further comprising:
   based on the diagnosis at least in part, estimating future financial expenditures related to the patient.

10. The computer-readable medium of claim 1, further comprising, repeating the steps in claim 1 against data from a plurality of patients, each associated with corresponding drug history data, so as to provide a diagnosis for each of the plurality of patients; and,
   based on the diagnosis at least in part, determining drug utilization patterns for groupings of patients, the groupings of patients based on age, sex, or commonalities in drug usage or patterns of drug usage.

11. The computer-readable medium of claim 1, further comprising:
   repeating the steps in claim 1 against data from a plurality of patients, each associated with corresponding drug history data, so as to provide as diagnosis for each of the plurality of patients; and
aggregating a plurality of patients with the same diagnosis and determining past costs associated with that aggregate group of patients.

12. A computer-implemented system for determining a diagnosis for a patient based on at least the patient's drug history comprising:
   a database module containing at least: (1) the age and sex of the patient, and (2) the patient's drug history, the drug history including information defining at least two drugs the patient had previously received, and (3) a set of rules which define relationships between age and sex, drug history, and a diagnosis;
   a rules module, which applies rules from the database module against information indicative of the patient's age and sex data and the patient's drug history; and,
   a diagnosis assignment module, which assigns a probable medical diagnosis to the patient based on the rules module's application of rules.

13. The system of claim 12, wherein the database module additionally contains a hierarchy of diseases, the hierarchy based on either, or some combination of, the severity of the disease or the anticipated cost of treating the disease.

14. The system of claim 13, wherein the diagnosis assignment module assigns the probable medical diagnosis based on the hierarchy of diseases, such that the most severe disease, or the disease with the highest anticipated cost of treatment, is selected when there is more than one possible diagnosis based on the application of the rules.

15. A computer-based system having a memory and a processor which estimates a patient's future demand for healthcare services, comprising a software module running on a computer which analyzes a patient's drug history, and based on this analysis inters a current diagnosis based on the patient's drug history;
   wherein the analysis done by the software modules comprises applying at least one rule which defines a pattern of drug usage associated with a disease; and,
   wherein the at least one rule is applied to the patient's drug history based on a hierarchy of diseases, the hierarchy being a function, at least in part, of the severity of the disease to the patient's health, and the hierarchy of diseases is applied such that if the application of the rules yields a plurality of possible diseases, the most severe disease is associated with the patient.

16. A computer-implemented method comprising:
   receiving drug history data that identifies a plurality drugs taken by a patient;
   applying one or more drug diagnosis rules to the drug history data, the drug diagnosis rules defining relationships between drug history data and a possible diagnosis for the patient;
   determining a probable diagnosis for the patient based on the application of the one or more drug diagnosis rules; and,
   receiving data indicative of the patient's sex, and wherein the drug diagnosis rules additionally include relationships between the sex of a patient, drug history, and the possible diagnosis.

17. The computer-implemented method of claim 16, further comprising:
receiving data indicative of the patient's age, and wherein the drug diagnosis rules additionally include relationships between the age of a patient, drug history, and the possible diagnosis.

18. The computer-implemented method of claim 16, wherein determining a probable diagnosis additionally includes receiving a diagnosis hierarchy, the hierarchy a function of either diseases severity or cost of treatment, or some combination thereof, and where, if there are more than one possible diagnosis based on the application of the one or more drug diagnosis rules, selecting the diagnosis based on the hierarchy.

19. A computer-implemented method for inferring a patient's current diagnosis from a data set, comprising:
receiving patient indicative of age and sex data;
receiving drug history data that identities at least one drug taken by the patient;
applying one or more drug diagnosis rules to the patient age and sex data and the drug history data, the drug diagnosis rules defining relationships between drug history data, patient age and sex data, and a diagnosis;
receiving diagnosis hierarchy data that defines which disease should be inferred in the event that the application of the one or more drug diagnosis rules results in more than one possible current diagnosis; and,
inferring the current diagnosis for the patient based on the application of the one or more drug diagnosis rules, and the application of the diagnosis hierarchy.

* * * * *

UNITED STATES PATENT AND TRADEMARK OFFICE
CERTIFICATE OF CORRECTION

| | |
|---|---|
| PATENT NO. | : 8,579,811 B2 |
| APPLICATION NO. | : 11/532919 |
| DATED | : November 12, 2013 |
| INVENTOR(S) | : Jon Eisenhandler et al. |

Page 1 of 1

It is certified that error appears in the above-identified patent and that said Letters Patent is hereby corrected as shown below:

In the Specifications:

Column 6
Line 16; delete "the a" and insert --the-- therefor.

In the Claims:

Column 15
Claim 1, Line 4; delete "to;" and insert --to:-- therefor.

Column 16
Claim 11, Line 5; delete "provide as" and insert --provide a-- therefor.
Claim 15, Line 41; delete "inters" and insert --infers-- therefor.

Column 17
Claim 19, Line 18; delete "identities" and insert --identifies-- therefor.

Signed and Sealed this
Twenty-second Day of April, 2014

Michelle K. Lee
*Deputy Director of the United States Patent and Trademark Office*